United States Patent [19]
Burns et al.

[11] Patent Number: 5,463,910
[45] Date of Patent: Nov. 7, 1995

[54] MULTI-FUNCTION ASPIRATING DEVICE

[75] Inventors: Rickey D. Burns, Alpharetta; Drew F. Meincke; Bernhard H. Heitz, both of Woodstock, all of Ga.

[73] Assignee: AVL Scientific Corporation, Roswell, Ga.

[21] Appl. No.: 242,972

[22] Filed: May 16, 1994

[51] Int. Cl.$^6$ .................................................. G01N 35/10
[52] U.S. Cl. .................... 73/864.87; 73/864.21; 73/864.22
[58] Field of Search ............................ 73/864.21, 864.22, 73/864.87

[56] References Cited

U.S. PATENT DOCUMENTS

| | | | |
|---|---|---|---|
| 3,949,615 | 4/1976 | Stein et al. | 73/864.22 |
| 3,960,020 | 6/1976 | Gordon et al. | 73/864.22 |
| 4,217,780 | 8/1980 | O'Connell et al. | 73/864.22 |
| 4,302,421 | 11/1981 | Baker | 73/864.22 X |
| 4,343,766 | 8/1982 | Sisti et al. | 73/864.21 X |
| 4,434,672 | 3/1984 | Williamson et al. | 73/864.22 |
| 4,756,201 | 7/1988 | Uffenheimer | 73/864.83 |
| 4,927,603 | 5/1990 | Fischer et al. | 73/864.21 X |
| 4,965,045 | 10/1990 | Lillig et al. | 422/68.1 |
| 5,043,141 | 8/1991 | Wilson et al. | 73/864.87 X |
| 5,264,182 | 11/1993 | Sakagami | 73/864.21 X |
| 5,279,794 | 1/1994 | Sasao | 73/864.22 X |
| 5,413,686 | 5/1995 | Klein et al. | 204/299 R |

*Primary Examiner*—Thomas P. Noland
*Attorney, Agent, or Firm*—Watson, Cole, Grindle & Watson

[57] ABSTRACT

A housing pivotally supports a door which is interconnected with an arm carrying a hollow probe. A fillport module is slidable into operative position within the housing. The module supports a resilient fillport having an opening through which fluid passes. The opening has a tapered outer end for sealingly engaging a capillary tube. The probe is disposed within the opening and has an open outer end to receive fluid from a syringe. The probe is movable between an inner position where the outer end of the probe is within the opening when fluid is received from a capillary tube to an outer position where the outer end of the probe is disposed outwardly of the fillport when fluid is received from a syringe. A shoulder on the fillport sealingly engages the outer surface of the probe at all times, and a stop limits inward movement of the probe. A cleaner is carried by the door and is moved into sealing engagement with the fillport module so that a cleaning solution may be passed through the fillport and probe.

27 Claims, 5 Drawing Sheets

MULTI-FUNCTION ASPIRATING DEVICE

BACKGROUND OF THE INVENTION

The present invention relates to a multi-function aspirating device for use with medical instruments which are adapted to analyze fluid samples. An example is an instrument for use in the field of clinical hematology which is adapted to analyze blood samples from various patients. The fluid samples obtained from patients may be disposed in capillary tubes or syringes. It is therefore desirable to provide an aspirating device which is adapted to effectively aspirate fluids from either a capillary tube or a syringe. Prior art devices have been designed for such purposes but have proved to be unsatisfactory due to the requirement of using a special adapter in order to carry out the desired functions, or the construction has been complex and difficult to use.

The aspirating device must be capable of use with either capillary tubes or syringes, thereby providing two different functions. In addition, it is essential that the device also be provided with means for carrying out the function of effectively cleaning the components forming the fluid flow path for the fluid samples which are analyzed. Thorough cleaning of these components is necessary between uses of the device to prevent contamination of a succeeding sample by the residue of a preceding sample. In this manner, an accurate analysis of the fluid samples can be obtained with an associated analyzing machine.

It is accordingly a principal object of the invention to carry out the three above-described functions in a simple and effective manner with a construction that is economical to manufacture and yet which is durable and reliable in operation.

A further objective of the invention is to provide a construction wherein certain critical elements of the device may be quickly and easily replaced when necessary in such a manner that the replacement may be done by relatively unskilled personnel.

SUMMARY OF THE INVENTION

The present invention incorporates a unique construction wherein a fillport means is provided with an opening therethrough for receiving fluid samples. The opening is tapered from a large dimension at the outer end thereof to a smaller dimension in a direction toward the inner end of the opening. A capillary tube may be inserted through the outer end of the opening, and the tapered configuration of the opening ensures that the end of the capillary tube will sealingly seat on the wall of the opening even though the outer diameter of various capillary tubes may vary.

In order to receive samples from a syringe, a hollow probe means is disposed within the opening in the fillport means with the outer surface of the probe means continuously in sealing contact with the fillport means. An annular shoulder is formed on the fillport means and extends into the opening to engage the outer surface of the probe means at all times. The probe means is connected to the measurement chamber of an associated analyzing machine where the fluid sample is analyzed. When a fluid sample is aspirated from a capillary tube, the fluid passes through the opening into the probe means and thence to the analyzing machine. When it is desired to aspirate fluid from a syringe, the probe means is moved outwardly such that the open outer end of the probe means is disposed a substantial distance outwardly of the opening in the fillport means so that the probe means can receive a fluid sample directly from the syringe.

A door means is pivotally supported on a housing and is operatively connected to the probe means. In one position of the door means, the probe means is moved outwardly to cooperate with a syringe. In another position of the door means, the probe means is moved inwardly to a position where the open outer end of the probe means is disposed adjacent the inner end of the opening in the fillport means. In this position, the opening in the fillport means is adapted to receive a capillary tube so that a fluid sample many be aspirated from the capillary tube. In a third position of the door means, cleaning means is disposed in sealing relationship to the fillport means whereupon cleaning solution is passed through the opening and the probe means for thoroughly cleaning the device between uses thereof and preventing contamination of one fluid sample by another fluid sample.

The construction of the invention thereby permits the three basic functions discussed above to be effectively carried out while providing an arrangement which is economical to produce and yet is durable and reliable in operation.

In addition, a fillport module is provided which includes a sub-housing which can be readily mounted on or removed from the main housing of the device so that the module can be easily replaced when desired. This sub-housing supports key critical elements of the device including the fillport means and the probe means. The module sub-housing is retained in place on the main housing by retaining means which permits the module to be removed when desired so that a replacement module may be put in its place.

DESCRIPTION OF THE PREFERRED EMBODIMENT

Referring now to the drawings wherein like reference characters designate corresponding parts throughout the several views, there is shown in FIGS. 1 and 10–12 a housing formed of two interconnected components comprising a plastic molded member 20 and a stamped sheet metal side plate 22. Member 20 includes a top wall 21 joined to a back wall 24 and a side wall 26. A depending front wall 28 is joined to top wall 22 and is also joined to side wall 26. A first bottom wall 30 extends laterally from side wall 26 and joins with a sloping wall 32 which in turn joins with a second bottom wall joined to back wall 24.

A wall 40 extends laterally from side wall 26 and is joined with a hollow cylindrical boss 42. Three spaced hollow tapered bosses 44, 46 and 48 extend laterally from side wall 26. A further boss 50 extends laterally from side wall 26 and includes a reduced end portion 51. Boss 50 also includes a ridge portion 52 extending therealong which serves as a stop means as hereinafter described. Plate 22 has a plurality of recessed portions 42', 44', 46' and 48' each of which has a hole formed therethrough so that the holes are directly aligned with bosses 42, 44, 46 and 48 respectively when the plate is positioned against the open side of housing member 20. When plate 22 is so positioned, it is substantially flush with the edges of housing member 20, and the plate is secured in operative position to close off the open side of housing member 20 by four screws 54 which extend through the openings in recesses in plate 22 and are threaded into the open ends of the bosses 42, 44, 46 and 48 on housing member 20.

Figures 10, 12:
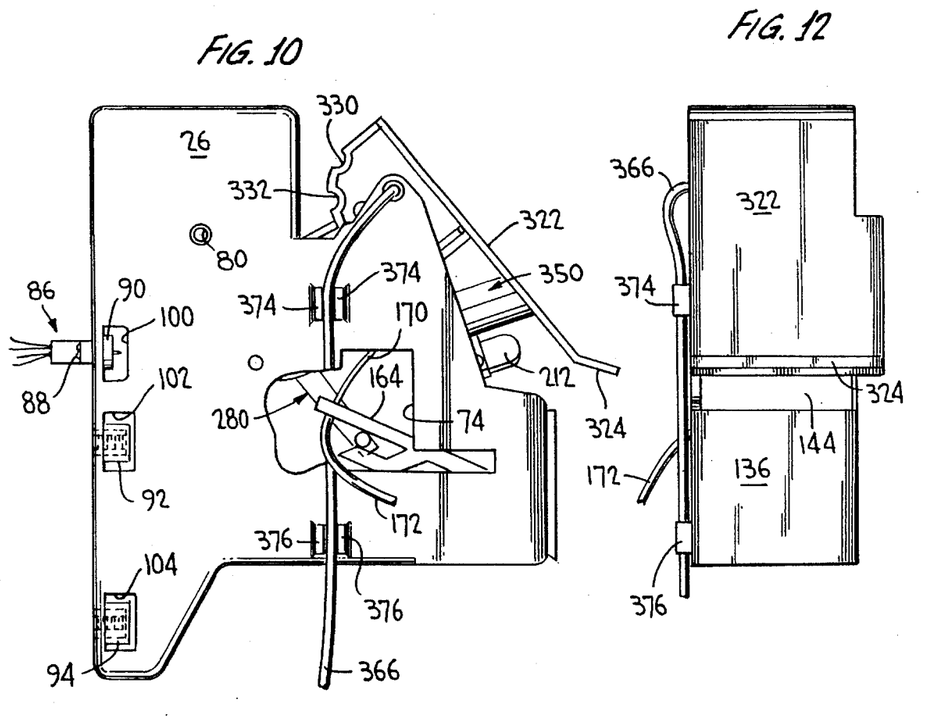
FIG. 10 is a side view of the assembled device.
FIG. 12 is a front view of the device shown in FIG. 10.
Figure 11:
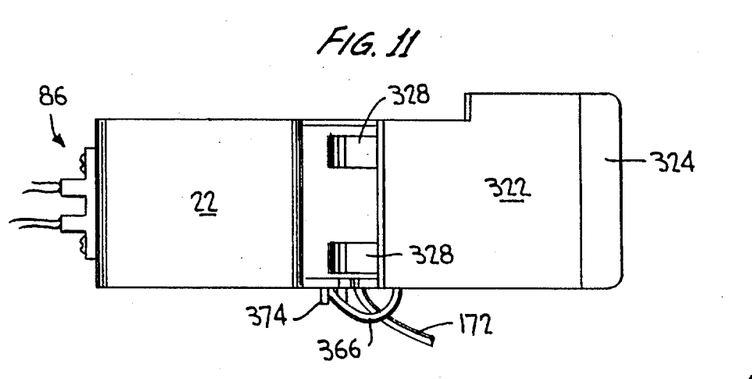
FIG. 11 is a top view of the device shown in FIG. 10.

Wall 40 of housing member 20 has a pair of holes 60 formed therethrough, and a pair of conventional ball detent devices 62 have a snap fit within holes 60. Plastic caps 64 are fitted on the lower ends of devices 62 for containing a suitable lubricant. A ramp means 66 has a sloping undersurface 68 which is adapted to cooperate with the probe arm means hereinafter described. A pair of spaced portions 70, shown as partly broken away, extend laterally from side wall 26 and define a guide slot 72 for a purpose hereinafter described. A protuberance 73 is formed on side wall 26 and extends into slot 72. A generally L-shaped cutout 74 is provided in wall 26 to receive a tubular member hereinafter described. A hole 78 is provided in side wall 26 for pivotally supporting one side of the door means, and a further hole 80, as seen in FIG. 10, is provided in the side wall 26 to pivotally support one side of the lifting arm means hereinafter described.

A notch 82 is provided in the rear wall 24 for receiving electrical wires. A slot 84 is provided in rear wall 24 for receiving a conventional optical switch generally indicated by reference numeral 86. The switch is held in position on the rear wall by a screw 88 which is threaded into a hole formed through a boss 90. A pair of mounting bosses 92 and 94 have metallic threaded members disposed therein for attaching the device to a suitable supporting structure which may, of course, be a fluid analyzing machine. As seen in FIG. 10, side wall 26 is also provided with three cutout areas 100, 102 and 104.

Plate 22 is provided with a further pair of recessed areas 110 and 112 each of which has a hole formed through the central portion thereof. A hole 114 is formed through an upper portion of the plate. The lower edge of plate 22 is provided with a laterally extending flange 116 extending from a notch 118 to the edge 120 thereof. The opposite edge 122 of the plate has formed thereon a tab 124 to which a grounding wire may be attached.

Figure 5:
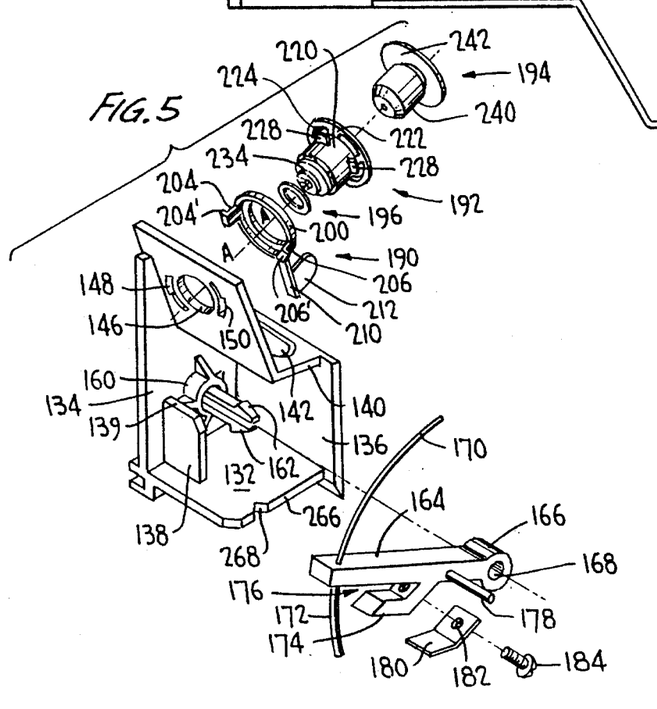
FIG. 5 is an exploded view of the fillport module.

Referring to FIG. 5, a fillport module is indicated generally by reference numeral 130 and comprises a unit which may be readily replaced or cleaned when desired. The module includes an integral molded sub-housing having a lower wall 132 which joins with a side wall 134 and a front wall 136. A wall 138 joined to the bottom wall and side wall includes a sloping upper edge 139 which serves as a stop means to limit movement of the probe means hereinafter described. The sub-housing includes a horizontal wall 140 joined to the front wall and the side wall and having a depression 142 formed in the upper surface to serve as a drip tray to collect any sample fluid which may fall from the fillport means or the probe means. The sub-housing includes a sloping upper front wall 144 having a hole 146 and a pair of bayonet slots 148 and 150 formed therethrough.

The sub-housing includes a boss 160 having a pair of spaced resilient prongs 162 extending therefrom. A probe arm means 164, which may be formed of a suitable metallic substance such as aluminum, has an enlarged end 166 having a bore 168 therethrough which receives the prongs 162 so that the probe arm means is mounted for pivotal movement about an axis extending midway between said prongs. The enlarged tips of the prongs ensure that the probe arm means is retained in position on the prongs.

The opposite end of the probe arm means has a hole formed therethrough, and a hollow probe means 170 is fixed in the hole by suitable adhesive means so that the probe means is carried by the probe arm means. An electrical connection is made between the probe means and the probe arm means by a suitable electrically conductive epoxy. The probe means may comprise a stainless steel hypodermic needle bent to a specific radius. The probe means extends along an arc having its center at the pivot axis of the probe arm means. The probe means extends through the probe arm means as seen in FIG. 5, the portion of the probe means extending below the probe arm means as seen in this figure having a plastic tube 172 frictionally engaged therewith. The tube passes through the L-shaped slot 74 in housing member 20 when the module is in place and is connected to a vacuum producing means of an associated fluid analyzing machine.

The probe arm means includes an integral portion 174 which is spaced from the remainder of the probe arm means to define a slot 176. A laterally extending finger 178 is press fitted into a suitable hole provided in the probe arm means. An angled metal tab 180 is provided for connection to a grounding wire. The tab has a hole 182 formed therethrough which receives a screw 184 threaded into a threaded hole 186 formed through the probe arm means. A serrated metal washer may be disposed between tab 180 and screw 184 to insure proper electrical contact between the screw and the tab.

Retainer ring means 190 is adapted to support mounting cup means 192 which in turn serves to mount fillport means 194. A plastic washer 196 is provided for a purpose hereinafter described. The retainer ring means is an integral molded plastic component and includes an annular ring portion 200 disposed around an axis A—A and which joins with an annular collar portion 202 extending radially inwardly of the ring portion. The collar portion defines a central opening which receives the mounting cup means 192. The retainer ring means includes a pair of diametrically opposite portions 204 and 206 which extend from ring portion 200, the outer ends of portions 204 and 206 having radially outwardly extending parts 204' and 206' respectively. Portions 204 and 206 are initially inserted through the large ends of bayonet slots 148 and 150, and then the retainer ring means is turned so that portions 204 and 206 are disposed in the smaller ends of the bayonet slots. The large ends of the bayonet slots allow the portions 204 and 206 along with the parts 204' and 206' to pass therethrough in a direction parallel with axis A—A, whereas parts 204' and 206' prevent removal of the retainer ring means in such a direction when portions 204 and 206 are in the smaller ends of the bayonet slots.

Figure 1:
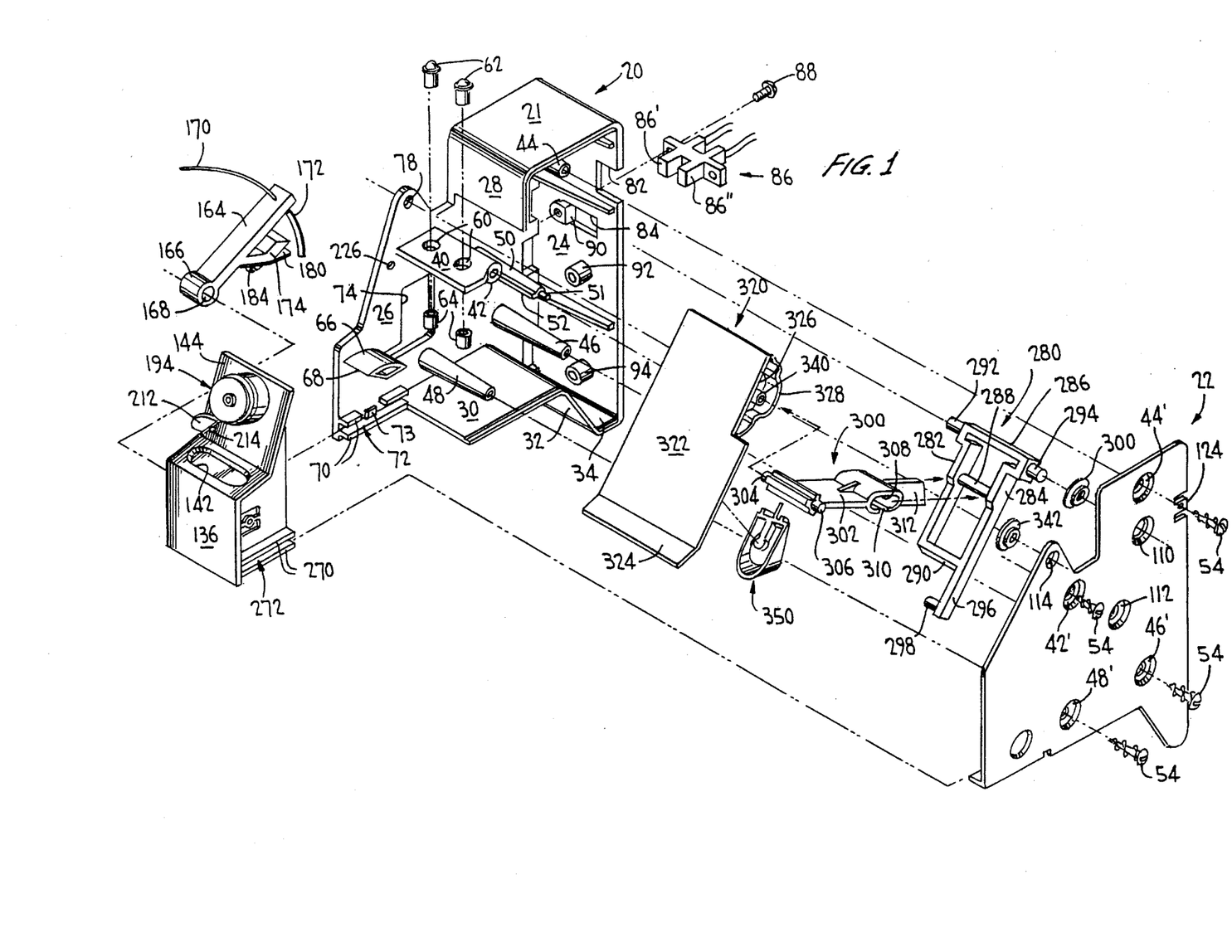
FIG. 1 is an exploded view of the components of the invention.

The retainer ring means also includes a radially outwardly extending arm 210 having a flat enlarged part 212 disposed at the outer end thereof which is adapted to be grasped in the fingers of a person assembling or disassembling the fillport module. As seen in FIG. 1, the upper front wall 144 of the module has a projection 214 formed thereon which engages arm 210 after the retainer ring means has been rotated in a clockwise direction to move portions 204 and 206 into the smaller end of the bayonet slots, thereby holding the components connected to the retainer ring means in operative position. When it is desired to disassemble the fillport module, arm 214 can be manually forced over projection 214.

Referring to FIGS. 5 and 7–9, the mounting cup means 192 comprises an integral plastic molded component including a cylindrical body portion 220 having an annular flange 222 extending around one end thereof and having four spaced arcuate slots 224 formed therethrough. Four equally spaced arcuate tabs 226 extend radially inwardly from body portion 220. Four equally spaced flexible arcuate tabs 228 extend radially outwardly from body portion 220, these latter tabs being disposed in spaced relation to flange 222 and also being disposed in positions offset forty-five degrees from tabs 226. The opposite end of the mounting cup means defines an end wall 230 having a central hole 232 formed therethrough for receiving the probe means. A boss 234 is formed on the end wall and has a recess 236 of frusto-conical shape tapering to hole 232 so as to guide the probe means into the hole. Four equally spaced arcuate slots 238 are formed through end wall 230.

Figure 6:
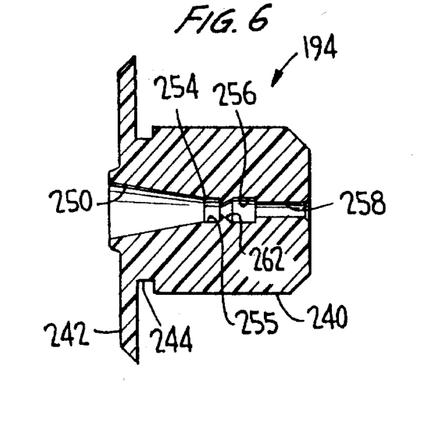
FIG. 6 is a sectional view through the fillport means.
Figure 7:
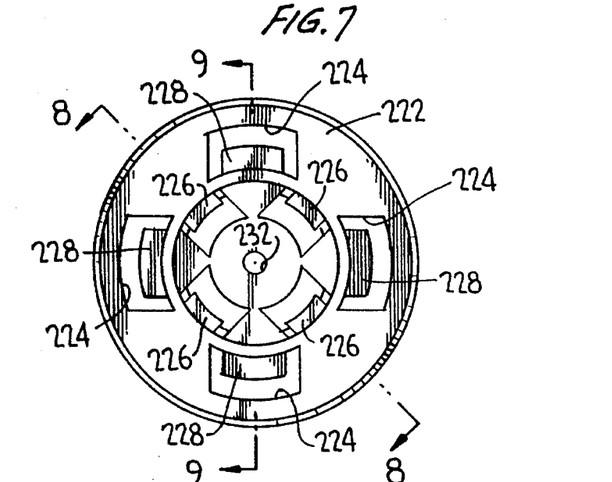
FIG. 7 is an end view of the support cup means.
Figure 8:
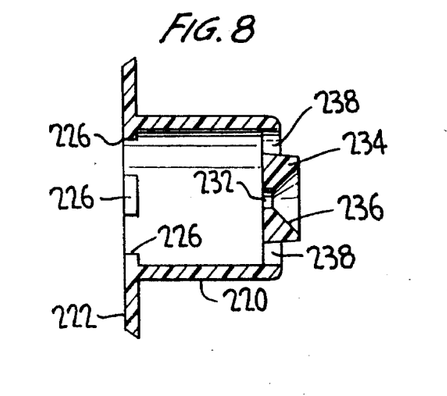
FIG. 8 is a sectional view taken on line 8—8 of FIG. 7.
Figure 9:
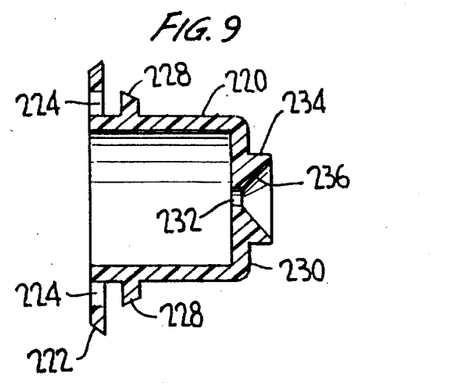
FIG. 9 is a sectional view taken on line 9—9 of FIG. 7.

Referring to FIG. 6, a longitudinal cross section is shown through fillport means 194. This is an integral component made of resilient elastomeric material such as silicone. A body portion 240 has a cylindrical outer surface, and an annular flange 242 extends radially outwardly thereof. A peripheral groove 244 is formed in the outer surface of the body portion and is adapted to receive the inwardly extending tabs 226 when the fillport means is inserted within the mounting cup means.

An opening is formed through the fillport means and includes a tapered wall portion 250 which tapers from the outer end 252 of the opening inwardly to a point 254 where it joins with a generally cylindrical wall portion 255. The opening further includes a generally cylindrical wall portion 256 which joins with a generally cylindrical wall portion 258 of smaller dimension extending to the inner end 260 of the opening. The fillport means includes between wall portions 255 and 256 an annular shoulder 262 which extends inwardly into the opening to effectively form an O-ring seal with the outer surface of the probe means. With this construction, the tapered wall portion 250 of the fillport means is adapted to sealingly engage in a fluid-tight manner capillary tubes of different outer diameters, and shoulder 262 ensures that a fluid-tight seal is maintained at all times with the outer surface of the probe means. When the probe means is in its innermost position, the outer open end of the probe means will extend slightly to the left of shoulder 262 as seen in FIG. 6 and short of point 254 so that the outer end of the probe means will not come into contact with a capillary tube at any time.

When assembling the fillport module, the fillport means 194 is snapped into placed within the support cup means with the tabs 226 seated within the groove 244 of the fillport means. Washer 196 is then placed on the support cup means in surrounding relationship to the boss 234. The washer closes off the slots 238 in the support cup means. The support cup means and the elements mounted thereon are then snapped into place on the retainer ring means with the collar portion 202 of the retainer ring means received between flange 222 and tabs 228 of the mounting cup means. The retainer ring means is then secured within hole 146 of the fillport module as previously described.

As seen in FIG. 5, lower wall 132 of the module has a side edge 266 having a notch 268 formed therein. As seen in FIG. 1, a pair of spaced portions 270 extend laterally from side wall 134 of the sub-housing and define a guide slot 272 therebetween. When the module is moved into operative position relative to the housing, edge 266 of bottom wall 132 of the housing is inserted in slot 72 in housing member 20, and flange 116 of the side plate 22 enters slot 272 of the module. The module is then pushed inwardly into its operative position which is limited by engagement of portions of the module with housing member 20 and plate 22.

The module is retained in this operative position by two different retaining means. The first retaining means comprises the interengagement of the protuberance 73 on housing member 20 with the notch 268 formed in the side edge of the bottom wall of the module. The second retaining means comprises a projection 276 on side wall 26 of housing member 20 as seen in FIG. 1. When the module is in operative position, projection 276 engages the upper front wall 144 of the module to hold the module in position. When it is desired to remove the module, a person can manually slide the module out of operative position when desired.

As seen in FIG. 1, a lifting arm means 280 comprises an integral molded plastic component including a pair of spaced side portions 282 and 284 which are joined by a top portion 286, a cross member 288 and a bottom portion 290. A pair of cylindrical journals 292 and 294 extend in opposite directions from side portions 282 and 284. Side portion 284 includes a downwardly extending end portion 296 which has a laterally extending boss 298 formed thereon which is received within the slot 176 of the probe arm means. Journal 292 is rotatably received within hole 80 in side wall 26 of housing member 20. Journal 294 has a conventional plastic shoulder washer 300 mounted thereon, washer 300 fitting within the hole in depression 110, whereby lifting arm means 280 is mounted for pivotal movement about an axis passing through the centers of journals 292 and 294.

A connecting arm means 300 comprises an integral molded plastic component including a body portion 302 having oppositely extending journals 304 and 306 formed at one end thereof for pivotally supporting the connecting arm means on door means hereinafter described. Body portion 302 defines an elongated slot 308 extending longitudinally of the connecting arm means. An opening 310 extends laterally across the body means to allow the cross member 288 of the lifting arm means to be snapped through opening 310 into slot 308 to thereby permit assembly and disassembly of members 280 and 300 when desired. Cross-member 288 disposed within the slot 308 for sliding movement therein to provide a lost motion connection between the lifting arm means and the connecting arm means.

Figures 2, 3:
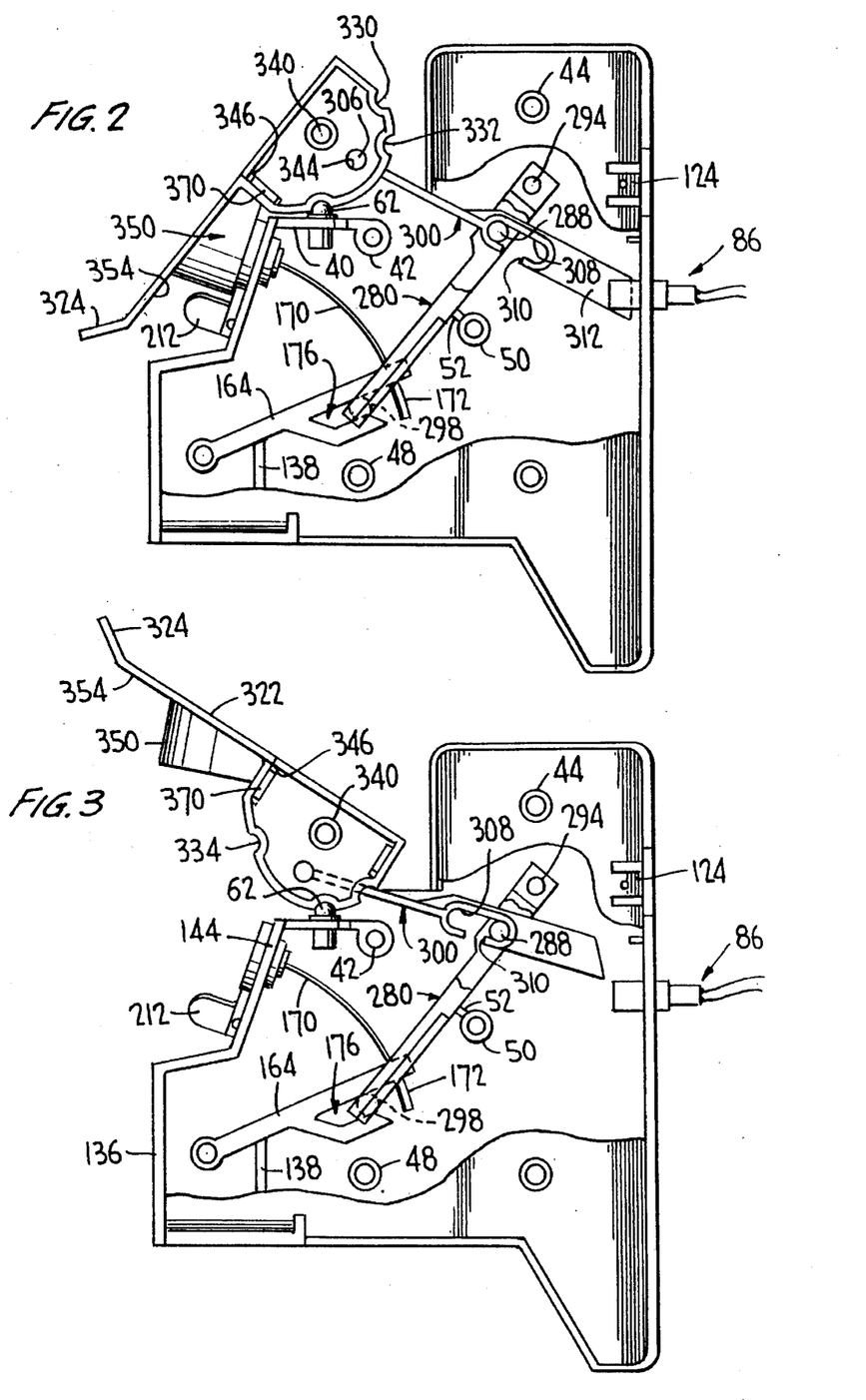
FIG. 2 is a view with the side plate broken away showing the door means in a first position.
FIG. 3 is a view with the side plate broken away showing the door means in a second position.

Lifting arm means 300 also includes an extension 312 which is adapted to be positioned between portions 86' and 86" of the optical switch 86 as seen in FIG. 1. The position of the extension is dependent on the position of the door means, and the particular position when the extension is between portions 86' and 86" is shown in FIG. 2. This particular position of the extension on the connecting arm means is detected by the optical switch to indicate that the door means is in its first position wherein the cleaning function can be carried out. In the other two positions of the door means, the optical switch will indicate that the door means has been moved from its first position.

The door means 320 comprises an integral molded plastic component including a flat body portion 322 having an angled lip 324 at one thereof to be manually engaged for manipulating the door means. A pair of similar spaced wall portions 326 extend at right angles to the undersurface of body portion 322. Wall portions 326 have oppositely directed flanges 328 extending at right angles to the lower edges thereof, these flanges riding on the ball detent devices 62. The flanges have three recesses 330, 332 and 334 formed therein to receive the ball detent devices to hold the door means in any one of three operative positions.

The wall portions 326 have oppositely directed hollow journals 340 for rotatably supporting the door means on the housing. One of the journals 340 is rotatably supported in hole 78 in the side wall 26 of housing member 20. The other of the journals 340 has a conventional plastic shoulder washer 342 disposed therearound which is disposed within the hole 114 in side plate 22. The door means is thereby rotatably supported between housing member 20 and plate 22. Wall portions 326 also each have a hole 344 formed therein for receiving the journals 304 and 306 to pivotally connect the connecting arm means to the door means. The dimensions of the components are such that the journals 304 and 306 may be manually snapped into place or manually removed when desired. Wall portions 326 also each have a slot 346 formed therein for supporting the cleaning means hereinafter described.

Figure 13:
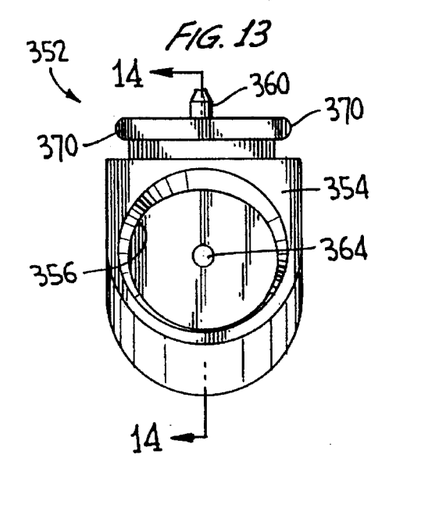
FIG. 13 is a top view of the cleaning means.
Figure 14:
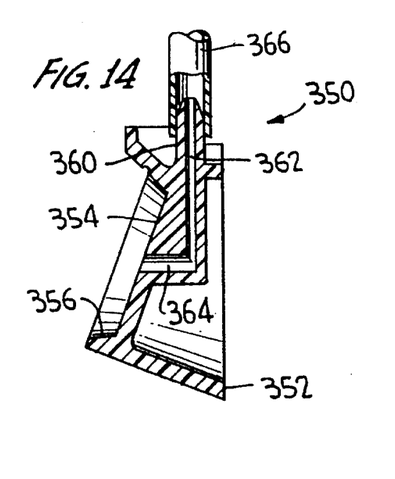
FIG. 14 is a sectional view taken on line 14—14 of FIG. 13.

The cleaning means 350 comprises an integral molded plastic component the details of which are shown in FIG. 13 and 14. An edge surface 352 lies in a plane and is adapted to fit snugly against the undersurface 354 of the door means. A main body portion 354 has a depression 356 therein which defines a recess for receiving the fillport means. When the door means is in the position shown in FIG. 2, the fillport means is disposed within the recess 356 and forms a fluid-tight seal with the flat bottom surface of the recess. A nipple 360 is formed on the main body portion and a passage 362 extends through the nipple and is in communication with a further passage 364 which opens into the center of the flat bottom surface of the recess. A suitable tube is frictionally engaged with the nipple and is connected to a cleaning fluid reservoir.

A pair of laterally extending lugs 370 are formed on opposite sides of the cleaning means, and these lugs are adapted to snap into the slots 346 of the door means to mount the cleaning means in the position shown. In this operative position, the tube 366 passes through one of the hollow journals 340 and as seen in FIG. 10 then passes downwardly through two pairs of retaining members 374 and 376 which tightly grip the tube to keep it in position relative to the housing.

OPERATION

Referring to FIG. 2, a first position of door means 320 is illustrated wherein the ball detent devices 62 are engaged with the recesses 334 disposed at opposite sides of the door means. In this position, the cleaning means 350 is disposed over the fillport means with the outer surface of the fillport means received within the recess 356 in the cleaning means and being in fluid tight sealing engagement with the flat bottom of the recess. In this position, vacuum may be applied to tube 172 to draw cleaning solution through tube 366 so that cleaning solution passes through the opening portions 250 and 255 into the open outer end of the probe means and then through tube 170 to a suitable waste container.

In the position shown in FIG. 2, the probe arm means 164 is contact with the upper sloping surface 139 of wall 138 of the fillport module, and the probe means 170 is disposed at its innermost position within the fillport means 194. The lifting arm means 280 is in contact with the ridge 52 on boss 50 with the boss 298 disposed within slot 176 of the probe arm means. The crossmember 288 of the lifting arm means is positioned at one end of the slot 308 of the connecting arm means 300. The extension 312 of the connecting arm means is disposed between the portions 86' and 86" of the optical switch 60 which causes the switch to indicate at a remote location that the door means is in the position shown in FIG. 2 with the cleaning means disposed in sealing relationship with the fillport means.

When it is desired to aspirate a fluid sample, a person grasps lip 324 of the door means and lifts the door means so that it rotates about eighty degrees to the position shown in FIG. 3 where the detent devices 62 are disposed within recesses 332 at opposite sides of the door means. In this position, a capillary tube containing a fluid sample to be aspirated can be inserted into the opening in the fillport means, and fluid may be drawn from the capillary tube into the fillport means and through the probe means and the associated tube to the analyzing chamber of an associated fluid analyzing machine. It is noted that when the door means moves from the position shown in FIG. 2 to that shown in FIG. 3, the lost motion connection between the connecting arm means and the lifting arm means causes the cross-member 288 to move to the opposite end of the slot 308 in the connecting arm means, while lifting arm means 280 and the probe arm means 164 remain in the same position.

Figure 4:
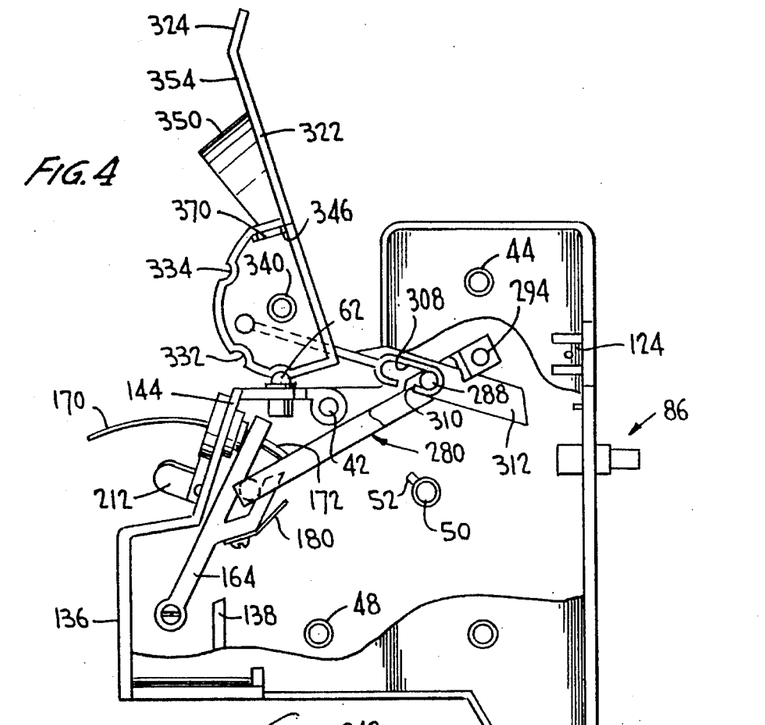
FIG. 4 is a view with the side plate broken away showing the door means in a third position.

When it is desired to aspirate a fluid sample from a syringe, the door means may be further rotated about thirty degrees to the position shown in FIG. 4 wherein the ball detent devices 62 are disposed within the recesses 330 disposed at opposite sides of the door means. As the door means moves into this position, the connecting arm means causes the lifting arm means and the probe arm means to move into the position shown which causes the probe means 170 to be moved outwardly so that the outer end of the probe means is spaced a substantial distance from the fillport means. In this position, the probe means is adapted to aspirate a fluid sample from a syringe upon application of a vacuum to the tube 172 so that the fluid sample may be drawn into the analyzing chamber of the associated analyzing machine.

After each aspiration of a fluid sample from either a capillary tube or a syringe with the door means in the position shown in FIG. 3 or FIG. 4 respectively, the door means is moved into the position shown in FIG. 2 so that a cleaning operation can be carried out. The door means provides a convenient means for manually positioning the device in any of the three operative positions thereof. It is also noted that in the position of the door means shown in FIGS. 3 and 4, the extension 312 of the connecting arm means is no longer disposed between the portions 86' and 86" of the optical switch means so that a signal is provided to suitable indicating means apprising an operator that the door means is no longer in the cleaning position shown in FIG. 2.

When it is desired to replace or clean the fillport module, the sub-housing is manually grasped and pulled outwardly of the main housing including elements 20 and 22. A cleaned or new fillport module including the probe arm means, the retainer ring means, the mounting cup means and the fillport means may then be slid into position with the edge 266 of the fillport module being received in the slot between portions 70 on wall 26 of the housing, while the flange 116 of the side plate 22 is received in the slot 272 between portions 270 on the fillport module. As the fillport module is inserted into operative position, the finger 178 on the probe arm means is adapted to engage the downwardly sloping surface 68 of the ramp means 66 to automatically align the probe arm means with the lifting arm means to ensure that boss 298 on the lifting arm means is received within the slot 176 of the probe arm means.

The invention has been described with reference to a preferred embodiment. Obviously, various modifications, alterations and other embodiments will occur to others upon reading and understanding this specification. It is our intention to include all such modifications, alterations and alternate embodiments insofar as they come within the scope of the appended claims or the equivalent thereof.

What is claimed is:

1. A multi-function aspirating device comprising, a housing, fillport means supported by said housing and including an opening formed therethrough for receiving a capillary tube containing a first fluid to be analyzed, a hollow probe means movably supported by said housing and being disposed within said opening, said probe means having an open outer end for receiving a second fluid to be analyzed, and means for moving said probe means between an inner position wherein said outer end of the probe means is disposed within said opening to an outer position wherein said outer end of the probe means is disposed a substantial distance outwardly of said opening to receive said second fluid to be analyzed from a syringe.

2. A device as defined in in claim 1 wherein said probe means has an outer surface, and sealing means for maintaining a fluid-tight seal between said fillport means and the outer surface of said probe means at all times.

3. A device as defined in claim 2 wherein said sealing means comprises a shoulder on said fillport means and extending inwardly into said opening to seal with the outer surface of said probe means.

4. A device as defined in claim 3 wherein said fillport means is formed of resilient material.

5. A device as defined in claim 1 wherein the opening through said fillport means includes an outer end and an inner end, said outer end receiving a capillary tube and tapering from a large dimension at said outer end to a smaller dimension in a direction toward said inner end.

6. A device as defined in claim 1 wherein said probe means is in sealing engagement with said fillport means, and stop means to limit inward movement of said probe means and establish said inner position to ensure that said probe means does not move out of sealing engagement with said fillport means.

7. A device as defined in claim 1 including cleaning means movably mounted on said housing, said cleaning means being movable into sealing relationship with said fillport means for passing cleaning solution through said opening and said probe means for thoroughly cleaning the device between uses thereof.

8. A multi-function aspirating device comprising a housing, a fillport module removably supported on said housing, retaining means for normally retaining said module on said housing, probe arm means pivotally supported on said module for pivotal movement about a pivot axis, hollow probe means supported on said probe arm means, a fillport mechanism removably supported on said module, said mechanism including fillport means having am opening formed therethrough and defining inner and outer ends, said opening tapering from a large dimension at said outer end to a smaller dimension in a direction toward said inner end, said probe means having an open outer end for receiving a fluid to be analyzed, said probe means being disposed within said opening and having an outer surface in fluid-tight sealing engagement with said fillport means adjacent said inner end of the opening at all times, and operating means supported by said housing for pivoting said probe arm means between a first position wherein said outer end of the probe means is in sealing engagement with said fillport means and a second position wherein said outer end of the probe means is disposed a substantial distance outwardly of said opening.

9. A device as defined in claim 8 wherein said fillport mechanism includes a retainer ring means, securing means for securing said retainer means to said module, mounting cup means removably supported by said retainer ring means, said fillport means being removably mounted on said mounting cup means.

10. A device as defined in claim 9 wherein said mounting cup means has a flange thereon and a plurality of spaced outwardly extending flexible tabs thereon, said retainer ring means defining an annular collar received between said flange and said flexible tabs to removably support said mounting cup means on said retainer ring means.

11. A device as defined in claim 9 wherein said mounting cup means has a plurality of inwardly extending tabs thereon, said fillport means having a peripheral groove formed thereon to receive said inwardly extending tabs to hold said fillport means in place on said mounting cup means.

12. A device as defined in claim 8 wherein said retaining means for said module includes a protuberance on said housing, said module having a lower wall with a side edge, said side edge having a recess therein for receiving said protuberance to retain the module in place relative to said housing.

13. A device as defined in claim 8 wherein said retaining means for said module includes a projection on said housing, said module having an upper front wall engaging said projection to retain the module in place relative to said housing.

14. A device as defined in claim 8 wherein said probe means extends along an arc having its center at said pivot axis of the probe arm means.

15. A device as defined in claim 8 including cleaning means movably mounted on said housing, said cleaning means being movable into sealing relationship with said fillport means for passing cleaning solution through said opening and said probe means for thoroughly cleaning the device between uses thereof.

16. A multi-function aspirating device comprising, a housing, fillport means supported by said housing and including an opening formed therethrough for receiving a capillary tube containing a first fluid to be analyzed, a hollow probe means being disposed within said opening, said probe means having an open outer end for receiving a second fluid to be analyzed, pivotally mounted probe arm means supported by said housing and carrying said probe means, door means pivotally supported by said housing, cleaning means supported on said door means, connecting arm means pivotally connected to said door means, lifting arm means pivotally connected to said housing and being operatively connected to said connecting arm means, said lifting arm means being operatively connected to said probe arm means, said door means in a first position causing said cleaning means to be sealingly associated with said fillport means to enable cleaning of the fillport means and probe means, said door means being movable to a second position to expose said fillport means to enable a capillary tube to be inserted into said opening, said door means being movable to a third position wherein said outer end of the probe means is disposed a substantial distance outwardly of said opening to receive said second fluid to be analyzed from a syringe.

17. A device as defined in claim 16 including detent means to hold said door means in each of its three operative positions.

18. A device as defined in claim 16 wherein said cleaning means includes a recess for receiving said fillport means and forming a fluid-tight seal therewith, and tube means for conveying cleaning solution to said recess and thence to said opening and probe means.

19. A device as defined in claim 16 wherein said lifting arm means is operatively connected to said connecting arm means by a lost motion connection.

20. A device as defined in claim 16 wherein said connecting arm means includes an extension, an optical switch means supported by said housing, said extension cooperating with said switch means to indicate when said door means is in said first position or one of the other two positions.

21. A device as defined in claim 16 wherein said lifting arm means has a cross member, said connecting arm means having a slot formed therein, said cross member being slidably disposed within said slot.

22. A device as defined in claim 16 wherein said lifting arm means has a laterally extending boss formed thereon, said probe arm having a slot formed therein and receiving said boss to provide an operative connection between said lifting arm means and said probe arm.

23. A device as defined in claim 16 wherein said probe arm means has a laterally extending finger thereon, said housing having a ramp means thereon with a sloping surface engageable with said finger.

24. A device as defined in in claim 16 wherein said probe means has an outer surface, and sealing means for maintaining a fluid-tight seal between said fillport means and the outer surface of said probe means at all times.

25. A device as defined in claim 24 wherein said sealing means comprises a shoulder on said fillport means and extending inwardly into said opening to seal with the outer surface of said probe means.

26. A device as defined in claim 16 wherein the opening through said fillport means includes an outer end and an inner end, said outer end receiving a capillary tube and tapering from a large dimension at said outer end to a smaller dimension in a direction toward said inner end.

27. A device as defined in claim 16 wherein said probe means is in sealing engagement with said fillport means, and stop means to limit inward movement of said probe means and establish said inner position to ensure that said probe means does not move out of sealing engagement with said fillport means.

* * * * *